Figure 1A:
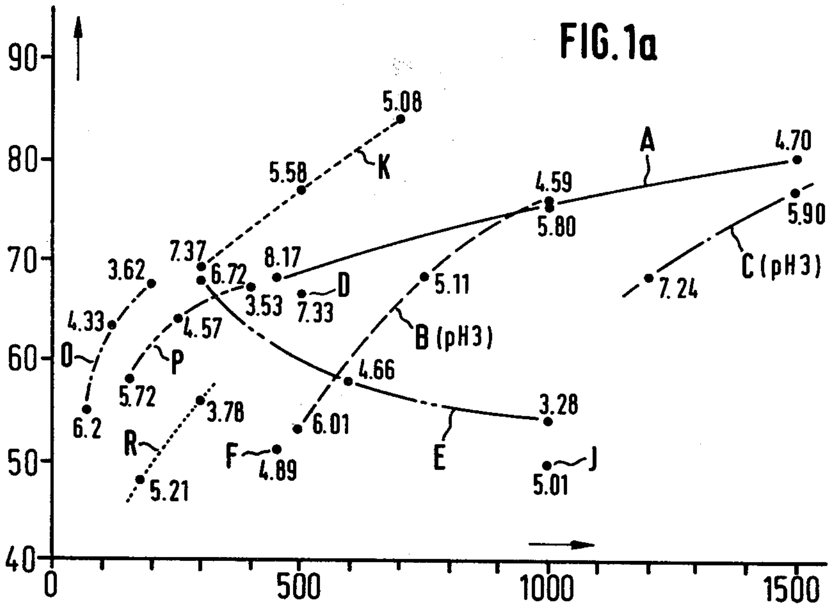

United States Patent [19]
Morawietz et al.
[11] 4,450,116
[45] May 22, 1984

[54] 3-OXYPROPYLENEIMINO-BIS-(METHYLENE PHOSPHONIC ACIDS) AND THEIR SALTS, PROCESS FOR THEIR MANUFACTURE AND THEIR USE

[75] Inventors: Hans-Joachim Morawietz, Kelkheim; Erich Hoffman; Johann Hanauer, both of Kriftel; Kurt Bauer, Kelsterbach, all of Fed. Rep. of Germany

[73] Assignee: Hoechst Aktiengesellschaft, Fed. Rep. of Germany

[21] Appl. No.: 398,097

[22] Filed: Jul. 14, 1982

[30] Foreign Application Priority Data

Jul. 21, 1981 [DE] Fed. Rep. of Germany ....... 3128755

[51] Int. Cl.$^3$ ............................ C07F 9/36; C22B 1/00
[52] U.S. Cl. .................................. 260/502.5 E; 75/2; 260/501.12
[58] Field of Search ...................... 260/502.5 E, 501.12

[56] References Cited

U.S. PATENT DOCUMENTS

| | | | |
|---|---|---|---|
| 3,298,956 | 1/1967 | Irani et al. | 260/502.5 E |
| 3,346,488 | 10/1967 | Lyons et al. | 260/502.5 E |
| 3,718,603 | 2/1973 | Mitchell | 260/502.5 E |
| 3,723,347 | 3/1973 | Mitchell | 260/502.5 E |
| 3,974,209 | 8/1976 | Mitchell | 260/502.5 E |
| 3,976,589 | 8/1976 | Mitchell | 260/502.5 E |

FOREIGN PATENT DOCUMENTS 605638 4/1978 U.S.S.R. .

OTHER PUBLICATIONS

Translation into German attached.

*Primary Examiner*—J. E. Evans
*Attorney, Agent, or Firm*—Connolly and Hutz

[57] ABSTRACT

3-Alkoxypropylenimino-bis-(methylene phosphonic acids) of the formula

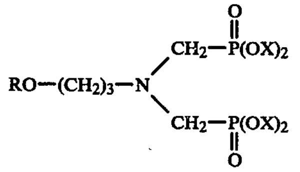

wherein R is straight-chain or branched alkyl or alkenyl each having from 2 to 20, preferably 2 to 10, carbon atoms, aryl, preferably phenyl or aralkyl, preferably benzyl, and X is hydrogen, an alkali metal, alkaline earth metal, ammonium, alkylammonium or polyalkylenepolyammonium ion, preferably a sodium, potassium or ammonium ion, a process for their manufacture and their use as collector in the flotation of non-sulfidic ores.

2 Claims, 8 Drawing Figures

3-OXYPROPYLENEIMINO-BIS-(METHYLENE PHOSPHONIC ACIDS) AND THEIR SALTS, PROCESS FOR THEIR MANUFACTURE AND THEIR USE

The present invention relates to new 3-oxypropyleneimino-bis-(methylene phosphonic acids) and their salts, to a process for their manufacture and to their use especially as flotation auxiliary, particularly in the case of tinstone.

It is known that the flotation process is a widely employed separation method for mineral raw materials, which comprises separating the valuable matter in minerals from unvaluable matter. To prepare the mineral raw material to the flotation process, the precrushed ore is subjected to dry grinding, preferably to wet grinding, until an adequate grain size is reached, this grain size depending on the one hand on the degree of intergrowth of the ore, that means on the size of the different mineral species in the ore body, and on the other hand on the grain size of the minerals to be subjected to flotation, which may greatly vary with the individual minerals. Tin ores have to be ground generally to a grain size of about 100% smaller than 150-100 μm. The ore is further prepared to the flotation process, unless it has been subjected to wet grinding, by suspending it in water. In the case of ores having a high portion of mineral slime, which may originate, for example, from clay minerals (montmorillonite, kaolinite, talcum and so on) it may be a very important step of the preparation to flotation to separate said mineral slime (<5-10 μm) by decantation in hydroseparators or with the aid of hydrocyclones, since said mineral slime may act in very defavorable manner on the selectivity of the flotation process and may render it uneconomic due to an extremely high consumption of reagents involved therewith. This aplplies to a great number of tin ores as well.

A further step of the preparation to the flotation process consists in adding flotation reagents which act on the minerals for varying periods of time. This applies in particular to the hydrophobization of the mineral to be subjected to flotation by a so-called collector or by a combination of several collectors. A great number of collectors for non-sulfidic minerals (oxhydril collectors) form themselves a froth suitable for flotation owing to their surface-active character. In the case of other ores it may be necessary to develop the froth by special reagents, called frothers or to modify said froth in adequate manner. Suitable flotation frothers are alcohols having from 4 to 10 carbon atoms in the hydrocarbon chain, polypropylene glycols, polyethylene or polypropylene glycol ethers, terpene alcohols (pine oils) and cresylic acids. If required, further modifying reagents are added, for example regulators for the pH which frequently acts in decisive manner on the flotation result, activators for the mineral to be recovered with the froth or compressants for the minerals which are undesired in the froth and, if desired, dispersing agents.

Since the compounds according to the invention are used in the first place as collectors, it should be mentioned that said collectors serve to hydrophobize the valuable minerals in the ore, so as to render them capable of attaching themselves to the ascendant air bubbles in the pulp. The valuable minerals are transported to the surface of the pulp by said air bubbles, where they are retained and collected in the froth formed. The mineralized froth may be stripped from the surface of the pulp, whereby the valuable minerals are separated from the unvaluable minerals.

It is further known in the art to separate tinstone from unvaluable minerals by flotation while employing different collector reagents, depending on the type of ore used. Appropriate tinstone collectors for ores containing gangue minerals that are not hydrophobized by anionic oxhydril collectors are in most cases monocarboxylic acids, in particular unsaturated long-chain fatty acids (for example tall oils), fatty alkyl sulfates or fatty alkyl sulfonates and mono-/di-phosphoric acid esters. Ores to be floated in more difficult manner, that means ores containing gangue minerals having a high flotation capacity, require more selective products such as arsonic acids, phosphonic acids and hydroxamic acid as well as sulfosuccinic acid derivatives and their salts.

The following compounds amongst the known collectors have proved to be particularly selective, that means to have a specific affinity to tinstone:

para-tolylarsonic acid 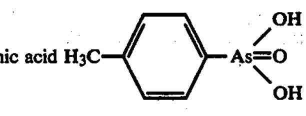 (I)

(cf. O. Neunhoeffer in "Metall und Erz," 1943, page 174 and French Pat. No. 881,935), 2-phenylethylenephosphonic acid, also designated as styrene phosphonic acid, which is considered as the most selective collector for tinstone at the present time

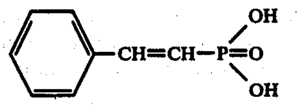 (II)

(cf. German Pat. No. 2,343,460 and Pat. No. 76,974 of the German Democratic Republic), tetrasodium-N-(1,2-dicarboxyethyl)-N-octadecylsulfosuccinamate

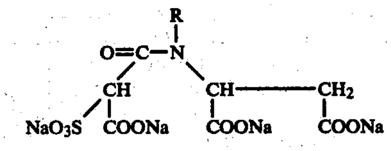 (III)

(cf. U.S. Pat. No. 2,438,092; British Pat. No. 1,110,643).

Russian patent specification No. 605,638 further proposes N-substituted imino-bis-methylene phosphonic acids of the formula

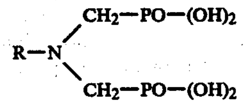 (IV)

wherein R is alkyl, alkenyl or cycloalkyl, as tinstone collectors.

It has now been found that the result of the flotation of non-sulfidic ores, in particular of tinstone, is distinctly improved both as regards the metal yield in the concentrate (froth) and the selectivity reflected by the metal contents of the concentrates by using the 3-alkoxypropyleneimino-bis-(methylene phosphonic acid) according to the invention and its salts. The lower specific consumption expressed in g/t, as compared to collectors of similar selectivity or the higher selectivity should be outlined in particular.

Subject of the present invention therefore are 3-oxypropyleneimino-bis-(methylene-phosphonic acids) of the formula

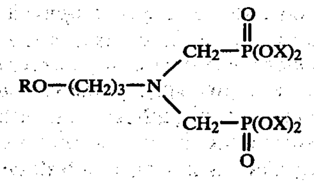

wherein R is straight-chain or branched alkyl or alkenyl each having from 2 to 20, preferably 2 to 10, carbon atoms, aryl, preferably phenyl or aralkyl, preferably benzyl, and X is hydrogen, an alkali metal, alkaline earth metal, ammonium, alkylammonium or polyalkylene polyammonium ion, preferably a sodium, potassium or ammonium ion.

These compounds are obtained by reacting an alkoxypropylene amine of the formula $$RO-(CH_2)_3-NH_2$$

wherein R is defined as above, with formaldehyde and phosphorous acid.

The alkoxypropylene diamines are obtained by reacting primary, secondary or tertiary alcohols ROH with acrylonitrile, followed by hydrogenation of the cyano group. Formaldehyde is used as aqueous solution, preferably at a concentration of 30–40% or in solid form as paraformaldehyde. The molar ratio of the individual reactants is 2–4, preferably 3–4, mols of formaldehyde and 2 mols of phosphorous acid per 1 mol of alkoxypropylene amine.

The compounds of the formula I are prepared by mixing alkoxypropylene amine, phosphorous acid and formaldehyde and heating the resulting mixture to a temperature above 50° C., preferably a temperature between 80° and 110° C. A pH of the reaction mixture below 4, more suitably below 2, must be guaranteed, in order to obtain optimum results. This is reached by adding acids that are capable of lowering the pH without impairing the reaction. Suitable acids for this purpose are hydrochloric acid, hydrobromic acid, sulfuric acid, phosporic acid and sulfonic acids.

The reaction can be carried out directly in aqueous medium, the phosphonic acid having relatively long alkyl chains, however, separating by crystallization towards the end of the reaction. To prevent this, a dissolving mediator may be added to the reaction mixture without impairing the reaction. Suitable dissolving mediators are polar organic solvents miscible with water at elevated temperature, for example alcohols having short alkyl chains such as n-propanol, iso-propanol, iso-butanol.

The alkali metal salts, alkaline earth metal salts, ammonium salts and amine salts are obtained in known manner by neutralization of the aqueous solutions or suspensions of the corresponding phosphonic acids with stoichiometric amounts of bases such as alkali or alkaline earth metal hydroxides, ammonia or amines such as mono-, di- or tri-ethanolamine, diethylene triamine or ethylene diamine. The salts obtained are distinguished in most cases by a higher solubility than the free acid.

The free acids precipitate from the reaction mixture because of their relatively low solubility and may be isolated by filtration. A concentration of the reaction mixture is recommended in the case of acids having a slightly better solubility. The salts may be further used direct in the form of their aqueous reaction solution. The salts may be isolated in solid form by spray-drying.

The 3-alkoxypropylenimino-bis-(methylene phosphonic acids) and their salts are also suitable for the treatment of water, where they prevent the formation of scalp and where they provoke a corrosion protection. They are further suitable as surfactants and active ingredients in detergents. Preferably, they are used, however, as collectors in flotation processes of non-sulfidic ores, for example of ores containing tungsten, niobium, tantalum or zirconium. The compounds according to the invention are particularly suitable as collectors in the flotation of tinstone.

The following examples illustrate the invention.

EXAMPLES I TO VIII 200 g of 35% hydrochloric acid, 164 g of phosphorous acid, 400 g of water and 1 mol of 3-alkoxypropylene amine are placed in a flask provided with a stirrer, a reflux condenser, a thermometer and a dropping funnel, the batch is heated to reflux temperature and 340 g of a 35% formaldehyde solution are added in the course of 2 hours at this temperature. Boiling at the reflux is continued for a further 3 hours. In the case of short-chain ether amines the reaction mixture is concentrated by distillation. Upon cooling the solution to 10° to 15° C., the 3-alkoxypropylenimino-bis-(methylene phosphonic acids) separate by crystallization, whereupon they are suction-filtered and dried.

The compounds listed in the following tables are obtained when proceeding in the above manner. When intended for use as flotation collectors for non-sulfidic ores, the compounds according to the invention may be added to the flotation pulp in the form of the free acid as well as preferably as aqueous solution or dispersion at concentrations of from 0.1 to about 10%. The quantity of the compounds according to the invention required to obtain an optimum metal yield is determined in decisive manner by the flotation capability of the ores which may greatly vary in some cases, by the grain size and naturally be the nature of the accompanying gangue minerals. This quantity may vary within wide limits as can be seen from the examples. In the case of tinstone, addition quantities of from 50 to 1,000 g of collector substance per ton of dry feedstock will be sufficient. It depends moreover on the conditions mentioned, whether the optimum quantity has to be added in one single portion at the beginning of the flotation process or in several portions in the course of the flotation process, the first portion being usually greater than the following portions.

The adsorption of the collectors according to the invention is normally so spontaneous that conditioning times of some minutes are sufficient. Longer treatment times may be required, however, in the case of ores that are more difficult to float. Longer treatment times may result in a reduction of the specific consumption.

A demonstrated by the flotation tests using the collectors according to the present invention, a second addition of collector in the afterpurification of the preconcentrate is not necessary, since the adsorption of tinstone is efficient enough to withstand several purification steps. This naturally does not exclude that there exist ores where a collector has to be added even in the afterpurification steps.

The froth cover produced on the flotation pulp by the collectors according to the invention is normally sufficient to reach an optimum flotation. Depending on the character of the ore and on its grain size distribution, upon the quality of the water available for the flotation process or on the water-soluble salts (electrolytes) contained in the ore, it may be advantageous to use an additional frother. The best known frothers have been mentioned hereinbefore. If there has been added a constant quantity of a very defined frother (polypropylene glycol) in all of the examples listed below, this has been done to suppress the influence of the greatly varying froth formation of the different collectors on the flotation result, that means to bring out more clearly the originary selectivity and activity of the collectors. The fact that there has always been used one polypropylene glycol does not exclude the use of other types of frothers in conjunction with the collectors according to the invention. Alternatively, the collectors according to the invention can naturally be used without an additional frother.

As can be seen from the following examples, the selectivity of the collectors according to the invention for tinstone is so high that the use of regulating substances, such as activators or depressants, can be dispensed with in many cases. This does not exclude naturally that substances that are suitable as depressants for the unvaluable gangue minerals may be used to improve the selectivity of the collectors according to the invention. The following substances are usually employed in the flotation of tin ores as gangue depressants: Na-silicate (sodium water glass), Na-fluoride, Na-silicofluoride, sodium salts of ethylene diamine tetraacetic acid, oxalic acid, tartaric acid, citric acid and so on (cf. Pat. No. 94 966 of the German Democratic Republic and E. Wottgen: Steigerung der Effektivität der Zinnsteinflotation durch Weiterentwicklung der Reagenzienführung und Anwendung einer Erzvorbehandlung [Improvement in the efficiency of the tinstone flotation by a further development concerning the use of the reagents and by subjecting the ore to a preliminary treatment], Freiburger Forschungsheft A 621, 1980). Gangue depressants have been deliberately omitted in the following examples, which demonstrate the superiority of the collectors according to the invention, in order to bring out the originary activity and in particular the originary selectivity of the collectors according to the invention as compared with the conventional tinstone collectors. Only pH regulators have been used.

A pH regulation, for example by means of sulfuric acid, is important, as the pH has a decisive influence on the efficiency and selectivity of all tinstone collectors, including thus also the collectors according to the invention. A pH of about 5 has proved optimal for all of the ores examined, both as regards the preflotation and the afterpurification of the preconcentrates. Only in one case it has been necessary to increase the pH to 6 in order to counteract a disagreable froth formation at lower pH values. In this respect, the collectors according to the invention correspond to the other phosphonic acids used for tinstone flotation processes (loc. cit.); however, they differ substantially and in very positive manner, for example, from the succinamates mentioned and also from hydroxamic acids, which exhibit their full action only at a pH below 3, in a very acid medium, where considerable corrosion problems occur. Said optimal pH of 5–6 for the preflotation and after purification of the preconcentrates and intermediates refers to the ores examined, that means it is quite possible that a lower or higher pH may be appropriate for other ores. It is also common practice in tinstone flotation to carry out the preflotation at a higher pH (for example of 5) and to lower the pH gradually in the following purification steps (for example to 4) in order to improve the selectivity.

Sulfide minerals (ferrous sulfite $FeS_2$, magnetic pyrite FeS, arsenical pyrites, copper pyrites $CuFeS_2$), which are present in nearly all tin ores, are usually and necessarily removed for reasons of selectivity by means of the usual sulfhydril collectors (xanthates, dithiophosphates and so on) and a frother, prior to subjecting the tinstone to flotation. This process applies also to the tinstone flotation using the collectors according to the invention, since said collectors likewise hydrophobize at least partially heavy metal-containing and nonferrous metal-containing sulfide minerals. In the following examples a sulfide flotation could be dispensed with, since there was used in all cases the original feedstock for the tinstone flotation from industrial flotation plants, which had been subjected to a sulfide flotation. This original feedstock had been cleared from sludge in all cases.

For comparison with the collectors according to the invention there were used both the conventional collectors used in the industry and the substances according to the above-cited Russian Pat. No. 605,638 with similar chemical constitution.

All of the collectors used in the following examples were designated as acids for reasons of simplicity, although the products were used in all cases in the form of completely neutralized salts so as to be dosed more easily.

The following designations were used for the collectors in the following examples, tables and diagrams:

1. Comparative Substances 1.1 Conventional products used on a large scale

Collector A=2-Phenylethylene phosphonic acid, styrene phosphonic acid

Collector B=Tetrasodium-N-(1,2-dicarboxyethyl-N-octadecyl-sulfosuccinamate

Collector C=Oleylhydroxamic acid 1.2 Products according to Russian Pat. No. 605,638

Collector D=n-Hexylimino-bis-methylene phosphonic acid

Collector E=n-Octylimino-bis-methylene phosphonic acid

Collector F=2-Ethylhexylimino-bis-methylene phosphonic acid

Collector G=Isononylimino-bis-methylene-phosphonic acid

Collector H=Tallow fatty alkylimino-bis-methylene phosphonic acid

Collector I=Oleylimino-bis-methylene phosphonic acid

2. Collector K=n-Butoxypropylenimino-bis-methylene phosphon acid

Collector L=n-Hexylpropylenimino-bis-methylene phosphonic acid

Collector M=n-Octyloxypropylenimino-bis-methylene phosphonic acid

Collector N=2-Ethylhexyloxypropylenimino-bis-methylene phosphonic acid

Collector O=Isononyloxypropylenimino-bis-methylene phosphonic acid

Collector P=n-Octyl-/n-decyloxypropylenimino-bis-methylene phosphonic acid

Collector R=n-Decycloxypropylenimino-bis-methylene phosphonic acid

EXAMPLE 1

A South-African tin ore having a tin content of 1.26% was subjected to flotation in the form of an original feedstock from an industrial flotation plant, from which the sulfide minerals had been removed by flotation and which had been cleared from sludge (separation of the mineral slime <10 μm). The material had the following grain size distribution:

| grain size (μm) | weight % |
|---|---|
| +125 | 0.4 |
| 125–90 | 2.5 |
| 90–63 | 7.1 |
| 63–25 | 40.2 |
| –25 | 49.8 |
| | 100.0 |

The pH of the flotation pulp was regulated by means of 1% sulfuric acid and kept constant by automatic addition via a pH-meter. A pH of 5 for the preflotation and purification flotation was chosen for all phosphonic acids, consequently, as well for the products according to the invention. In the case of the collector B the pH for the preflotation had to be lowered to 3 and for the purification flotation even to 2.5. In the case of the collector C a pH of 3 proved optimal both for the preflotation and for the purification flotation.

All collectors were used in the form of sodium salts as 1% solutions which had been prepared with demineralized water. The quantities added which are listed in the table refer to the active substance. A conditioning time of one minute proved sufficient for all collectors. In all tests there were added 30 g/t of polypropylene glycol (as 1% solution) as additional frother in order to substantially exclude a distortion of the collecting activity due to the different froth formation of the individual collectors. The conditioning time for the frother was likewise 1 minute. An addition of regulating reagents was dispensed with for the above reasons.

In the case of all collectors the flotation process proceeded so quickly that three minutes were sufficient for the preflotation step. The first purification flotation, which was carried out without the addition of further reagents, required two minutes only. Further purification steps were omitted because of the low quantities of concentrate.

The preflotation was effected by using a Denver laboratory flotation machine of type "Sub-A" containing a 2.5 l cell. The purification flotation was carried out in a 1 liter steel cell.

The type of collectors used can be seen from Table 1, where there are likewise listed the flotation results. The flotation results for the most important collectors are moreover represented in graphic manner in the accompanying figures.

The first graphs (FIGS. 1*a* and 1*b*) demonstrate the tin yield in dependence on the quantities of additive both for the preconcentrate and for the concentrate subjected to one afterpurification step. The numerals located at the points along the yield curves indicate the tin contents of the corresponding concentrates. FIGS. 1*a*–4*a* represent the results obtained in the preflotation and FIGS. 1*b*–4*b* represent the results obtained upon one afterpurification step.

Figure 1B:
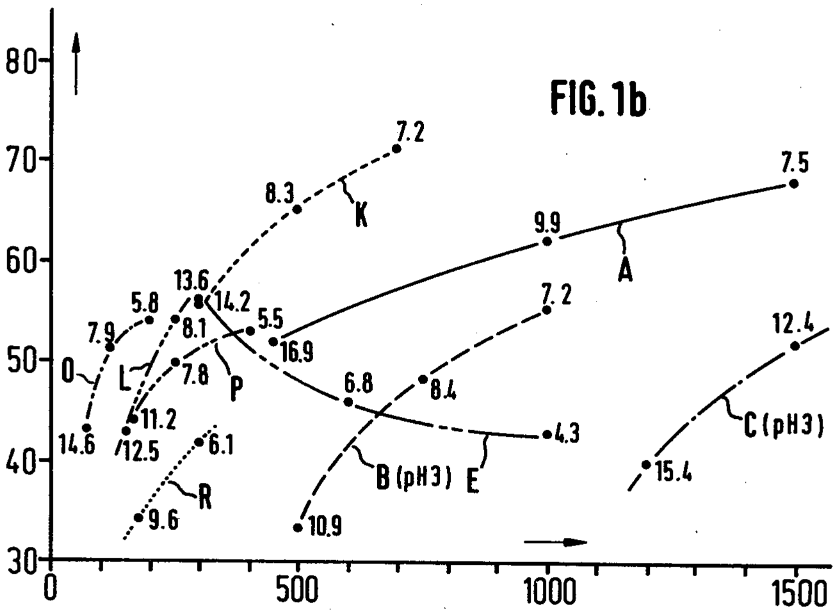

It can be clearly seen from FIGS. 1*a* and 1*b* that the collector K according to the invention has a far greater activity than the tinstone collector A, B and C in use in the industry without impairing the selectivity.

Collector K is also superior over the alkylimino-bis-methylene phosphoric acids (collectors D to J).

EXAMPLE 2

This example was also carried out using the original flotation feedstock of a South-African preparation plant for tin ore, said ore being, however, far more difficult to float than the ore of Example 1. Its Sn content was 1.0%. The flotation feedstock had the following grain size distribution:

| grain size (μm) | weight % |
|---|---|
| +90 | 1.0 |
| 90–63 | 4.2 |
| 63–25 | 37.7 |
| –25 | 57.1 |
| | 100.0 |

The flotation conditions corresponded to those of Example 1, except that the pH for the preflotation and for the purification flotation using the collectors according to the invention had to be set at 6 in order to obtain an absorptive appropriate froth. The pH for the collector A used for comparative reasons had likewise to be set at 5 as in Example 1.

Figure 2A:
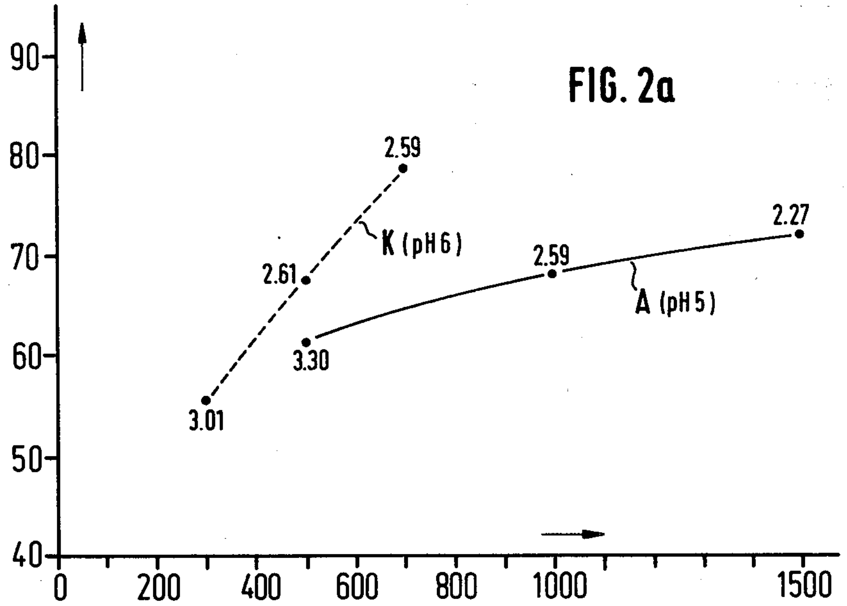
Figure 2B:
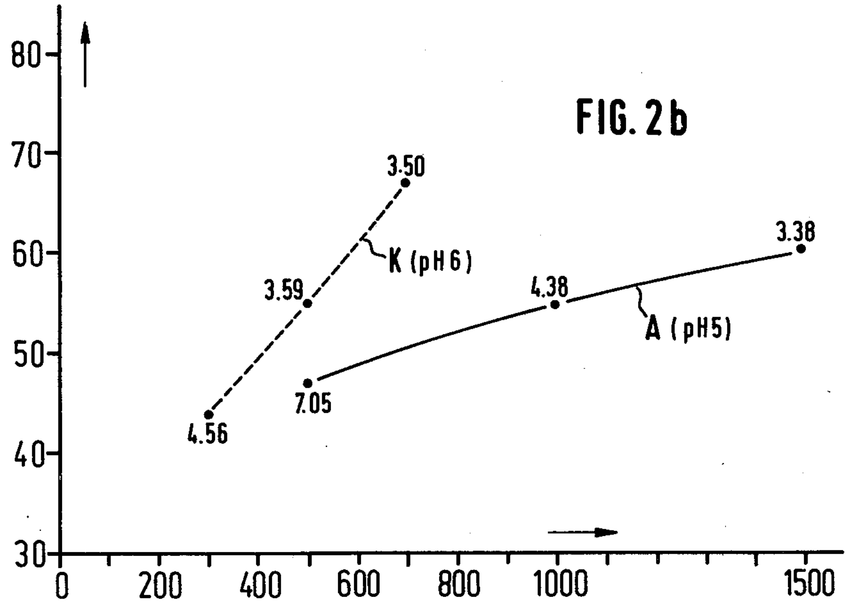

The results obtained can be seen from Table 2 and from the graphs (FIGS. 2*a* and 2*b*). In this case, too, the collector K is superior over the collector A, while not impairing the selectivity. The steep slope of the yield curve for the collector K is very striking, while the curve for the collector A is very plane. It may be assessed therefrom that the consumption of collector K is less than half of the consumption of collector A.

EXAMPLE 3

This example was carried out using a tin of Australian origin which had a Sn content of 1.35%. This tin ore was likewise used in the form of the original flotation feedstock of an industrial plant and had the following grain size distribution:

| grain size (μm) | weight % |
|---|---|
| +90 | 0.3 |
| 90–63 | 3.2 |
| 63–25 | 32.0 |
| –25 | 64.5 |
| | 100.0 |

The flotation conditions corresponded exactly to those of Example 1.

Figure 3A:
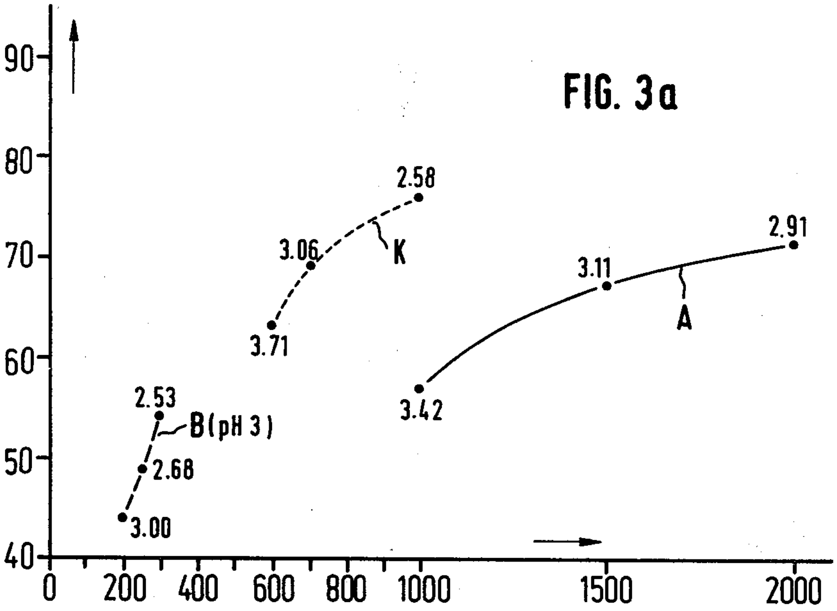
Figure 3B:
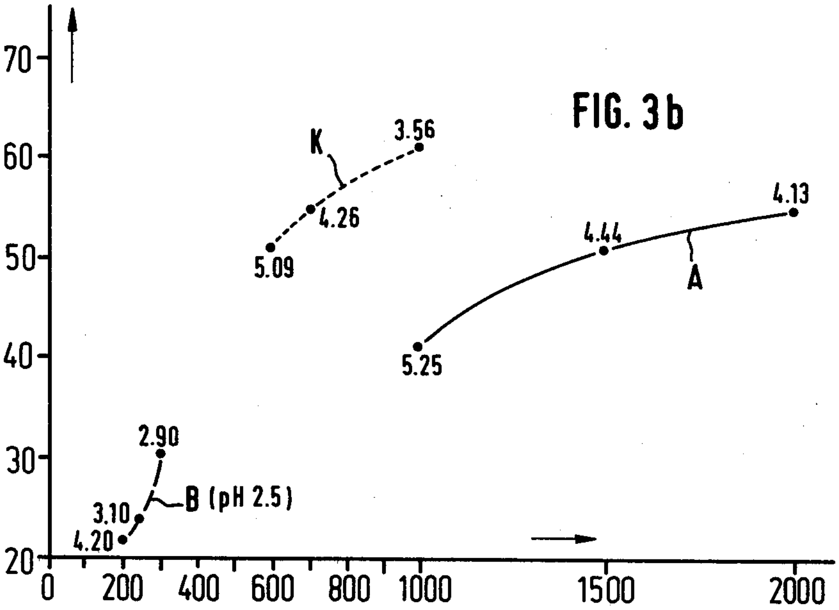

The results are summarized in Table 3 and represented graphically in FIGS. 3*a* and 3*b*.

In this case, too, it can be clearly seen that the collector K according to the invention has a distinctly greater activity than the collector A. It can moreover be seen by the Sn contents determined for the individual concentrates, which are indicated at the corresponding points or the yield curves, that the selectivity of the collector K is at least equal to that of the collector A, or even superior over that of the collector A. The collector B likewise used for comparative reasons is somewhat more active tahn the collector K, however, its selectivity is greatly lower, which can be read off from the Sn contens. It had to be floated at a far lower pH of about 2.5.

EXAMPLE 4

This example uses an English tin ore (original flotation feedstock of an industrial treatment plant) which had a relatively low Sn content of 0.52% and such a high degree of intergrowth that it had to be crushed to far smaller grain size than the ores specified in the foregoing examples. The flotation feedstock had the following grain size distribution:

| grain size (μm) | weight % |
|---|---|
| +90 | 1.0 |
| 90–63 | 2.3 |
| 63–25 | 19.9 |
| −25 | 76.8 |
| | 100.0 |

-continued

Figure 4A:
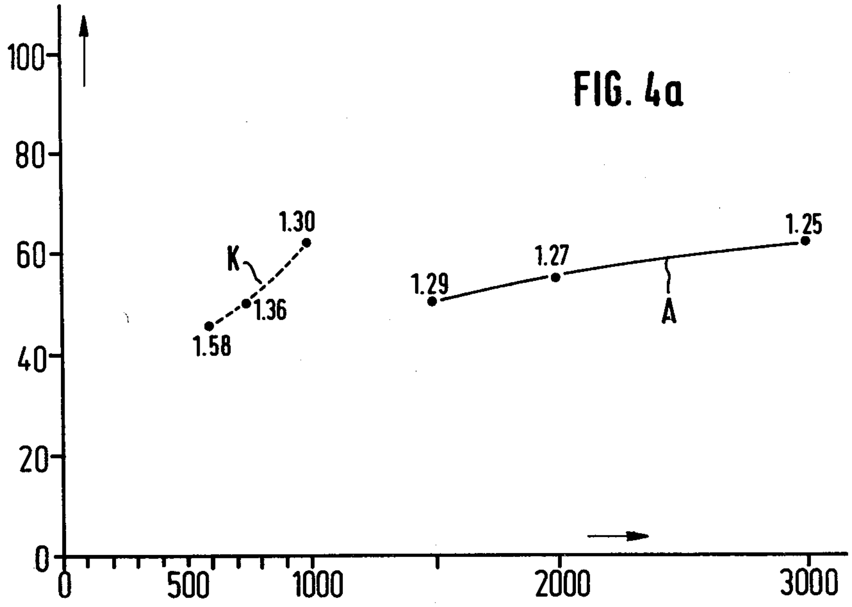
Figure 4B:
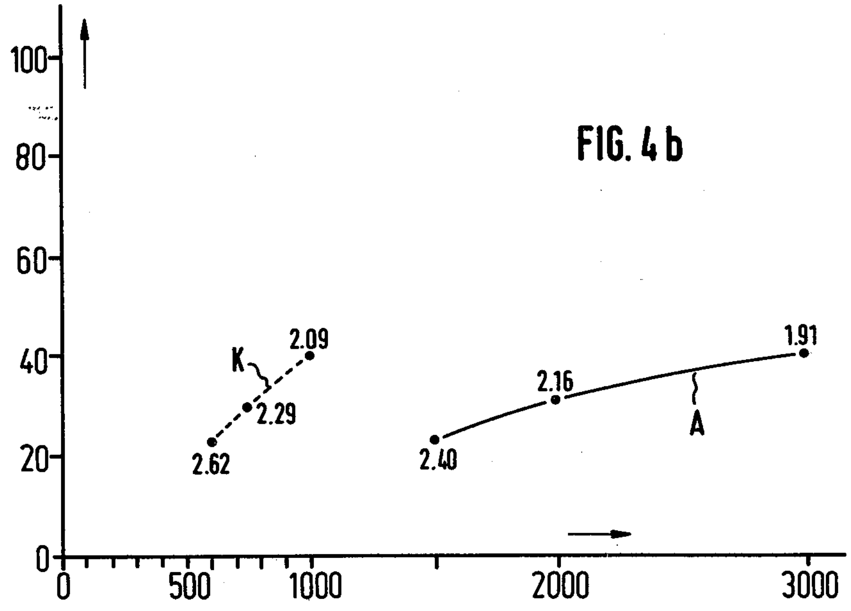

Owning to the finer granulation of the flotation feedstock, a considerably greater quantity of collector had to be added, while operating at the same flotation conditions as in the foregoing examples (cf. Table 4 and the graph [FIGS. 4*a* and 4*b*]). The collector K according to the invention had to be added in a quantity of 1,000 g/t in order to reach a Sn-yield of somewhat more than 60%, while a quantity of from 100 to 500 g/t was sufficient in the foregoing examples to obtain the same yield. The collector A had to be added in a quantity of as great as 3,000 g/t. It can be seen by the Sn contents that the collector K according to the invention is superior over the collector A.

TABLE 1 a

| Designation of reagent | g/t | Flotation feedstock Sn % | Preconcentrate weight % | Preconcentrate Sn-content- % | Preconcentrate Sn-output % | Upon one afterpurification: concentrate weight % | concentrate Sn-content % | concentrate Sn-output % | middlings weight % | middlings Sn-content % | middlings Sn-output % | abatement weight % | abatement Sn-content % | abatement Sn-output % |
|---|---|---|---|---|---|---|---|---|---|---|---|---|---|---|
| Collector A | 450 | 1.31 | 11.0 | 8.17 | 68.2 | 4.0 | 16.9 | 51.8 | 6.9 | 3.1 | 16.4 | 89.0 | 0.47 | 31.9 |
| | 1000 | 1.31 | 17.1 | 5.80 | 76.0 | 8.3 | 9.9 | 62.4 | 8.9 | 2.0 | 13.6 | 82.9 | 0.38 | 24.0 |
| | 1500 | 1.33 | 22.7 | 4.70 | 80.3 | 12.1 | 7.5 | 68.3 | 10.6 | 1.5 | 12.0 | 77.3 | 0.34 | 19.7 |
| Collector B | 500 | 1.21 | 10.7 | 6.01 | 52.9 | 3.7 | 10.9 | 33.4 | 7.0 | 3.4 | 19.5 | 89.3 | 0.64 | 47.1 |
| | 750 | 1.27 | 17.0 | 5.11 | 68.5 | 7.3 | 8.4 | 48.7 | 9.6 | 2.6 | 19.8 | 83.0 | 0.48 | 31.5 |
| | 1000 | 1.29 | 21.4 | 4.59 | 76.2 | 10.0 | 7.5 | 55.8 | 11.4 | 2.3 | 20.4 | 78.6 | 0.39 | 23.8 |
| Collector C | 1200 | 1.27 | 12.0 | 7.24 | 68.7 | 3.3 | 15.4 | 40.6 | 8.7 | 4.1 | 28.1 | 88.0 | 0.45 | 31.3 |
| | 1500 | 1.29 | 16.9 | 5.90 | 76.9 | 5.4 | 12.4 | 52.2 | 11.4 | 2.8 | 24.7 | 83.1 | 0.36 | 23.1 |
| | 2300 | 1.30 | 21.6 | 5.01 | 83.1 | 8.2 | 8.9 | 56.5 | 13.3 | 2.6 | 26.7 | 78.4 | 0.28 | 16.9 |
| Collector D | 500 | 1.24 | 11.4 | 7.33 | 67.3 | 6.0 | 11.1 | 53.9 | 5.4 | 3.1 | 13.4 | 88.6 | 0.46 | 32.7 |
| F | 450 | 1.18 | 12.3 | 4.89 | 51.0 | 3.6 | 8.3 | 25.1 | 8.7 | 3.5 | 25.9 | 87.7 | 0.66 | 49.1 |
| G | 300 | 1.23 | 11.2 | 7.23 | 65.5 | 5.1 | 13.2 | 54.1 | 6.1 | 2.3 | 11.4 | 88.8 | 0.48 | 34.6 |
| E | 300 | 1.28 | 12.9 | 6.72 | 67.9 | 5.3 | 13.6 | 56.0 | 7.7 | 2.0 | 12.0 | 87.1 | 0.47 | 32.1 |
| E | 600 | 1.27 | 15.8 | 4.66 | 58.1 | 8.6 | 6.8 | 46.2 | 7.2 | 2.1 | 11.9 | 84.2 | 0.63 | 41.9 |
| E | 1000 | 1.21 | 20.0 | 3.28 | 54.2 | 12.1 | 4.3 | 43.2 | 7.8 | 1.7 | 11.0 | 80.1 | 0.69 | 45.8 |
| J | 1000 | 1.18 | 11.7 | 5.01 | 49.6 | 4.5 | 8.8 | 33.9 | 7.1 | 2.6 | 15.7 | 88.4 | 0.67 | 50.4 |
| H | 1000 | 1.17 | 10.5 | 4.96 | 44.3 | 3.9 | 8.5 | 27.9 | 6.6 | 2.9 | 16.4 | 89.5 | 0.73 | 55.7 |
| Collector K | 300 | 1.28 | 12.1 | 7.37 | 69.7 | 5.0 | 14.2 | 55.9 | 7.1 | 2.5 | 13.8 | 87.9 | 0.44 | 30.3 |
| | 500 | 1.30 | 18.0 | 5.58 | 77.3 | 10.2 | 8.3 | 65.3 | 7.8 | 2.0 | 12.0 | 82.0 | 0.36 | 22.7 |
| | 700 | 1.40 | 23.2 | 5.08 | 84.1 | 13.9 | 7.2 | 71.5 | 9.3 | 1.9 | 12.6 | 76.8 | 0.29 | 15.9 |
| Collector L | 150 | 1.38 | 14.1 | 5.55 | 56.5 | 4.8 | 12.5 | 43.0 | 9.3 | 2.0 | 13.5 | 85.9 | 0.70 | 43.5 |
| | 250 | 1.40 | 19.4 | 4.63 | 64.2 | 9.3 | 8.1 | 54.1 | 10.0 | 1.4 | 10.1 | 80.7 | 0.62 | 35.8 |
| | 350 | 1.33 | 24.0 | 3.57 | 64.6 | 13.9 | 5.3 | 55.4 | 10.1 | 1.2 | 9.1 | 76.0 | 0.62 | 35.5 |
| Collector M | 100 | 1.24 | 13.6 | 5.24 | 57.4 | 4.3 | 11.7 | 41.0 | 9.2 | 2.2 | 16.4 | 86.5 | 0.61 | 42.6 |
| | 150 | 1.25 | 17.4 | 4.33 | 59.5 | 6.9 | 8.3 | 45.5 | 10.4 | 1.7 | 14.0 | 82.6 | 0.62 | 40.5 |
| | 300 | 1.27 | 23.3 | 3.33 | 60.9 | 11.5 | 5.0 | 46.4 | 11.8 | 1.7 | 14.5 | 76.7 | 0.65 | 39.1 |
| Collector O | 75 | 1.20 | 10.7 | 6.20 | 55.3 | 3.6 | 14.6 | 43.4 | 7.1 | 2.0 | 11.9 | 89.3 | 0.60 | 44.7 |
| | 120 | 1.20 | 17.6 | 4.33 | 63.5 | 7.8 | 7.9 | 51.2 | 9.8 | 1.5 | 12.3 | 82.4 | 0.53 | 36.5 |
| | 200 | 1.24 | 22.9 | 3.62 | 66.9 | 11.5 | 5.8 | 54.1 | 11.3 | 1.4 | 12.8 | 77.2 | 0.53 | 33.1 |
| Collector P | 160 | 1.24 | 12.6 | 5.72 | 58.2 | 4.8 | 11.2 | 43.8 | 7.8 | 2.3 | 14.4 | 87.4 | 0.59 | 41.8 |
| | 250 | 1.29 | 18.0 | 4.57 | 63.8 | 8.2 | 7.8 | 49.3 | 9.9 | 1.9 | 14.5 | 82.0 | 0.57 | 36.2 |
| | 400 | 1.27 | 24.2 | 3.53 | 67.2 | 12.3 | 5.5 | 53.1 | 11.9 | 1.5 | 14.7 | 75.8 | 0.55 | 32.8 |
| Collector R | 180 | 1.15 | 10.6 | 5.21 | 47.9 | 4.1 | 9.6 | 34.4 | 6.4 | 2.4 | 13.5 | 89.4 | 0.67 | 52.1 |
| | 300 | 1.19 | 17.9 | 3.78 | 56.6 | 8.2 | 6.1 | 42.0 | 9.7 | 1.8 | 14.6 | 82.1 | 0.63 | 43.4 |
| | 600 | 1.18 | 23.2 | 3.12 | 61.1 | 11.8 | 4.6 | 45.7 | 11.4 | 1.6 | 15.4 | 76.8 | 0.60 | 38.9 |

TABLE 2

| Designation of reagent | g/t | Flotation feedstock Sn % | Preconcentrate weight % | Preconcentrate Sn-content- % | Preconcentrate Sn-output % | Upon one afterpurification: concentrate weight % | concentrate Sn-content % | concentrate Sn-output % | middlings weight % | middlings Sn-content % | middlings Sn-output % | abatement weight % | abatement Sn-content % | abatement Sn-output % |
|---|---|---|---|---|---|---|---|---|---|---|---|---|---|---|
| Collector A | 500 | 0.92 | 16.9 | 3.30 | 61.0 | 61.2 | 7.02 | 47.4 | 10.8 | 1.16 | 13.7 | 83.1 | 0.43 | 39.0 |
| | 1000 | 0.95 | 25.0 | 2.59 | 68.4 | 11.9 | 4.38 | 54.8 | 13.2 | 0.98 | 13.0 | 75.0 | 0.40 | 31.6 |
| | 1500 | 0.98 | 31.2 | 2.27 | 72.0 | 17.5 | 3.38 | 60.1 | 13.7 | 0.85 | 11.9 | 68.8 | 0.40 | 28.0 |
| Collector K | 300 | 0.95 | 17.6 | 3.01 | 55.8 | 9.2 | 4.56 | 44.2 | 8.4 | 1.31 | 11.6 | 82.4 | 0.51 | 44.2 |

TABLE 2-continued

| | | Flotation feedstock | Preconcentrate | | | Upon one afterpurification: concentrate | | | middlings | | | abatement | | |
|---|---|---|---|---|---|---|---|---|---|---|---|---|---|---|
| Designation of reagent | g/t | Sn % | weight % | Sn-content- % | Sn-output % | weight % | Sn-content % | Sn-output % | weight % | Sn-content % | Sn-output % | weight % | Sn-content % | Sn-output % |
| | 500 | 0.88 | 22.9 | 2.61 | 67.7 | 13.5 | 3.59 | 54.9 | 9.4 | 1.20 | 12.8 | 77.1 | 0.37 | 32.3 |
| | 700 | 0.87 | 26.4 | 2.59 | 78.8 | 16.6 | 3.50 | 67.0 | 9.8 | 1.05 | 11.8 | 73.6 | 0.25 | 21.2 |

TABLE 3

| | | Flotation feedstock | Preconcentrate | | | Upon one afterpurification: concentrate | | | middlings | | | abatement | | |
|---|---|---|---|---|---|---|---|---|---|---|---|---|---|---|
| Designation of reagent | g/t | Sn % | weight % | Sn-content- % | Sn-output % | weight % | Sn-content % | Sn-output % | weight % | Sn-content % | Sn-output % | weight % | Sn-content % | Sn-output % |
| Collector A | 1000 | 1.37 | 22.8 | 3.42 | 57.0 | 10.8 | 5.25 | 41.4 | 12.0 | 1.78 | 15.7 | 77.2 | 0.76 | 43.0 |
| | 1500 | 1.36 | 29.6 | 3.11 | 67.4 | 15.7 | 4.44 | 51.1 | 13.9 | 1.60 | 16.3 | 70.4 | 0.63 | 32.6 |
| | 1500 | 1.37 | 33.7 | 2.91 | 71.5 | 18.3 | 4.13 | 55.1 | 15.4 | 1.46 | 16.4 | 66.3 | 0.59 | 28.6 |
| Collector K | 600 | 1.28 | 22.0 | 3.71 | 63.3 | 12.9 | 5.09 | 51.1 | 9.1 | 1.75 | 12.4 | 78.0 | 0.60 | 36.4 |
| | 700 | 1.23 | 27.8 | 3.06 | 69.4 | 15.8 | 4.26 | 54.8 | 12.0 | 1.49 | 14.6 | 72.2 | 0.52 | 30.6 |
| | 1000 | 1.26 | 37.1 | 2.58 | 76.1 | 21.6 | 3.56 | 60.9 | 15.6 | 1.23 | 15.2 | 62.9 | 0.48 | 23.9 |
| Collector B | 200 | 1.36 | 23.8 | 3.00 | 44.2 | 6.9 | 4.20 | 21.8 | 17.0 | 1.80 | 22.4 | 76.2 | 1.00 | 55.8 |
| | 250 | 1.44 | 26.3 | 2.68 | 48.9 | 8.0 | 3.10 | 24.0 | 18.3 | 1.96 | 24.9 | 73.7 | 1.00 | 51.1 |
| | 300 | 1.44 | 31.2 | 2.53 | 54.7 | 10.6 | 2.90 | 30.5 | 20.6 | 1.69 | 24.1 | 68.8 | 0.95 | 45.3 |

TABLE 4

| | | Flotation feedstock | Preconcentrate | | | Upon one afterpurification: concentrate | | | middlings | | | abatement | | |
|---|---|---|---|---|---|---|---|---|---|---|---|---|---|---|
| Designation of reagent | g/t | Sn % | weight % | Sn-content- % | Sn-output % | weight % | Sn-content % | Sn-output % | weight % | Sn-content % | Sn-output % | weight % | Sn-content % | Sn-output % |
| Collector A | 1500 | 0.47 | 19.1 | 1.29 | 50.3 | 4.6 | 2.40 | 23.4 | 14.5 | 0.88 | 26.9 | 80.9 | 0.29 | 49.7 |
| | 2000 | 0.51 | 21.8 | 1.27 | 55.4 | 7.3 | 2.16 | 30.9 | 14.5 | 0.86 | 24.6 | 78.2 | 0.29 | 44.6 |
| | 3000 | 0.51 | 25.7 | 1.25 | 62.4 | 10.8 | 1.91 | 40.0 | 15.0 | 0.77 | 22.4 | 74.3 | 0.26 | 37.6 |
| Collector K | 600 | 0.52 | 15.1 | 1.58 | 46.0 | 4.7 | 2.62 | 23.7 | 10.4 | 1.11 | 22.2 | 84.9 | 0.33 | 54.1 |
| | 750 | 0.54 | 19.9 | 1.36 | 50.7 | 6.9 | 2.29 | 29.6 | 13.0 | 0.87 | 21.1 | 80.1 | 0.33 | 49.3 |
| | 1000 | 0.54 | 25.8 | 1.30 | 62.6 | 10.3 | 2.09 | 40.3 | 15.5 | 0.77 | 22.3 | 74.2 | 0.27 | 37.4 |

What is claimed is:

1. A compound of the formula

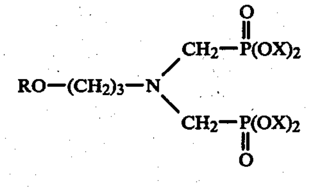

wherein R is straight-chain or branched alkyl having from 2 to 20 carbon atoms, and X is hydrogen, an alkali metal, alkaline earth metal, ammonium, alkylammonium or polyalkylene polyammonium ion.

2. A compound according to claim 1, wherein R in the formula is straight-chain or branched alkyl having from 2 to 10 carbon atoms, and X is a sodium, potassium or ammonium ion.

* * * * *